United States Patent [19]

Sumimoto et al.

[11] Patent Number: 4,797,492
[45] Date of Patent: Jan. 10, 1989

[54] POLYFLUOROALKYLISOXAZOLYLA-MINES

[75] Inventors: Shinzaburo Sumimoto, Ashiya; Ichiro Ishizuka, Toyono; Hiroyuki Kai, Koka; Shiro Ueda, Osaka; Akira Takase, Kobe, all of Japan

[73] Assignee: Shionogi & Co., Ltd., Osaka, Japan

[21] Appl. No.: 921,415

[22] Filed: Oct. 22, 1986

[30] Foreign Application Priority Data

Oct. 23, 1985 [JP] Japan ................. 60-238344

[51] Int. Cl.⁴ .......................... C07D 261/14
[52] U.S. Cl. .................... 548/245; 548/131; 548/133; 548/246; 558/440; 558/426; 558/449
[58] Field of Search .................. 548/245, 246

[56] References Cited

U.S. PATENT DOCUMENTS 4,268,679 5/1981 Lavanish .................. 548/247
4,471,123 9/1984 Varie et al. ............... 548/246
4,529,435 7/1985 Lavanish .................. 548/246

FOREIGN PATENT DOCUMENTS 0042732 12/1981 European Pat. Off. .
2230644 12/1974 France .

OTHER PUBLICATIONS

England et al. Chemical Abstracts, vol. 95, No. 9, 8/31/81, p. 704, Abs. No. 80012e.

Primary Examiner—Donald G. Daus
Assistant Examiner—E. Bernhardt
Attorney, Agent, or Firm—Wenderoth, Lind & Ponack

[57] ABSTRACT

A novel compound useful as an intermediate for synthesizing pesticides and medicines of the formula:

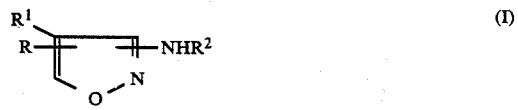

in which:
R is alkyl having plural florines; $R^1$ is hydrogen, alkyl, halogen or optionally substituted phenyl; and $R^2$ is hydrogen or alkyl, or a salt thereof.

23 Claims, No Drawings

POLYFLUOROALKYLISOXAZOLYLAMINES

FIELD OF THE INVENTION

The present invention relates to novel polyfluoroalkylisoxazolylamines which are useful as intermediates for synthesizing various medicines and other materials such as herbicides, fungicides and bactericides.

BACKGROUND OF THE INVENTION

Various herbicides, fungicides, bactericides etc. having isoxazolyl group have been provided. For example, U.S. Pat. No. 4,268,679, and Japanese Patent Laid Open Publication Nos. 56-131580 which is equivalent to U.S. Pat. No. 4,507,145, 57-31672 which is the equivalent of U.S. Pat. No. 4,336,264, 57-53484, equivalent to EP-A No. 44185, and 57-81467, equivalent to EP-A No. 49071 disclose various isoxazolylamines as their intermediates for synthesis. However, the prior art literature has not specifically disclosed isoxazolylamines having alkyl groups substituted by plural fluorine atoms.

SUMMARY OF THE INVENTION

Polyfluoroalkylisoxazolylamines of the present invention provide compounds of the formula (I):

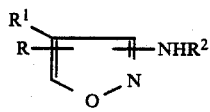

wherein R is an alkyl group having plural fluorine atoms; $R^1$ is hydrogen, alkyl, halogen or optionally substituted phenyl; and $R^2$ is hydrogen or alkyl, and salts thereof. Example of alkyl groups having plural fluorine atoms for R includes groups having 1-9 fluorine atoms and 1-4 carbon atoms, for example, trifluoromethyl, pentafluoroethyl, heptafluoropropyl and 2-(trifluoromethyl)propyl. Examples of $R^1$ alkyl groups includes $C_{1-5}$ alkyl, for example, methyl, ethyl, isopropyl and tert.-butyl. Examples of $R^1$ halogen groups includes chlorine, bromine, iodine, etc. . Examples of substituents for the substituted phenyl for $R^1$ includes halogen (i.e. fluorine, chlorine, etc.), $C_{1-4}$ alkyl (i.e. methyl, ethyl, isopropyl, etc.) and $C_{1-4}$ alkoxy (i.e. methoxy, isopropoxy, etc.). Two or more substituents may be present and they may form together, with the carbon atom to which they are attached a group such as methylenedioxy, ethylenedioxy, etc. . Examples $R^2$ alkyl groups include $C_{1-4}$ alkyl, for example, methyl, ethyl, isopropyl and tert.-butyl.

The group for R is located at either the 3- or 5-position of the isoxazole ring and the amino group is located at the other position.

Examples of the salts of the compound (I) include inorganic salts such as hydrochlorides, sulfates and nitrates and organic salts such as acetates, p-toluenesulfonates and methanesulfonates.

Typical examples of the compounds of the present invention are:

(1) the compound of the formula (I) in which R is trifluoromethyl located at the 5-position of the isoxazole ring and $R^1$ and $R^2$ are hydrogen;

(2) the compound of the formula (I) in which R is trifluoromethyl located at the 3-position of the isoxazole ring, $R^1$ is methyl and $R^2$ is hydrogen.

(3) the compound of the formula (I) in which R is trifluoromethyl located at the 5-position of the isoxazole ring, $R^1$ is methyl and $R^2$ is hydrogen;

(4) the compound of the formula (I) in which R is trifluoromethyl located at the 3-position of the isoxazole ring, $R^1$ is phenyl and $R^2$ is hydrogen;

(5) the compound of the formula (I) in which R is trifluoromethyl located at the 5-position of the isoxazole ring, $R^1$ is phenyl and $R^2$ is hydrogen;

(6) the compound of the formula (I) in which R is trifluoromethyl located at the 3-position of the isoxazole ring, $R^1$ is 4-fluorophenyl and $R^2$ is hydrogen;

(7) the compound of the formula (I) in which R is trifluoromethyl located at the 5-position of the isoxazole ring, $R^1$ is 4-fluorophenyl and $R^2$ is hydrogen.

(8) the compound of the formula (I) in which R is trifluoromethyl located at the 3-position of the isoxazole ring, $R^1$ is 4-chlorophenyl and $R^2$ is hydrogen;

(9) the compound of the formula (I) in which R is trifluoromethyl located at the 5-position of isoxazole ring, $R^1$ is 4-chlorophenyl and $R^2$ is hydrogen;

(10) the compound of the formula (I) in which R is trifluoromethyl located at the 3-position of the isoxazole ring, $R^1$ is 4-methylphenyl and $R^2$ is hydrogen;

(11) the compound of the formula (I) in which R is trifluoromethyl located at the 5-position of the isoxazole ring, $R^1$ is 4-methylphenyl and $R^2$ is hydrogen;

(12) the compound of the formula (I) in which R is trifluromethyl located at the 3-position of the isoxazole ring, $R^1$ is 4-methoxyphenyl and $R^2$ is hydrogen;

(13) the compound of the formula (I) in which R is trifluoromethyl located at the 5-position of theisoxazole ring, $R^1$ is 4-methoxyphenyl and $R^2$ is hydrogen;

(14) the compound of the formula (I) in which R is trifluoromethyl located at the 3-position of the isoxazole ring, $R^1$ is 3,4-dimethoxyphenyl and $R^2$ is hydrogen;

(15) the compound of the formula (I) in which R is trifluoromethyl located at the 5-position of the isoxazole ring, $R^1$ is 3,4-dimethoxyphenyl and $R^2$ is hydrogen;

(16) the compound of the formula (I) in which R is trifluoromethyl located at the 3-position of the isoxazole ring, $R^1$ is 3,4-methylenedioxyphenyl and $R^2$ is hydrogen;

(17) the compound of the formula (I) in which R is trifluoromethyl located at the 5-position of the isoxazole ring, $R^1$ is 3,4-methylenedioxyphenyl and $R^2$ is hydrogen;

(18) the compound of the formula (I) in which R is pentafluoroethyl located at the 3-position of the isoxazole ring and $R^1$ and $R^2$ are hydrogen;

(19) the compound of the formula (I) in which R is pentafluoroethyl located at the 5-position of the isoxazole ring and $R^1$ and $R^2$ are hydrogen;

(20) the compound of the formula (I) in which R is pentafluoroethyl located at the 3-position of the isoxazole ring, $R^1$ is methyl and $R^2$ is hydrogen;

(21) the compound of the formula (I) in which R is pentafluoroethyl located at the 5-position of the isoxazole ring, $R^1$ is methyl and $R^2$ is hydrogen;

(22) the compound of the formula (I) in which R is pentafluoroethyl located at the 3-position of the isoxazole ring, $R^1$ is phenyl and $R^2$ is hydrogen;

(23) the compound of the formula (I) in which R is pentafluoroethyl located at the 5-position of the isoxazole ring, $R^1$ is phenyl and $R^2$ is hydrogen;

(24) the compound of the formula (I) in which R is heptafluoropropyl located at the 5-position of the isoxazole ring and $R^1$ and $R^2$ are hydrogen;

(25) the compound of the formula (I) in which R is 2-(trifluoromethyl)propyl located at the 5-position of the isoxazole ring and $R^1$ and $R^2$ are hydrogen;

The compounds of the present invention can be prepared by the following procedure.

(a) They can be prepared by the reaction of a β-ketonitrile of the formula (II):

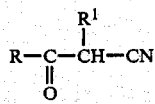

wherein R is alkyl having plural fluorine atoms and $R^1$ is hydrogen, alkyl or optionally substituted phenyl, with hydroxylamine, hydroxylamine hydrochloride, hydroxylamine sulfate, hydroxyurea, etc.

Preferably, this reaction is carried out in a solvent such as water, methanol, ethanol or ethylene glycol, neutralized with an alkali such as sodium bicarbonate, sodium carbonate or sodium hydroxide as necessary, at 60°–120° C. and then with the addition of 5–36% hydrochloric acid (1–2 eq.) at 60°–120° C.

(b) They can be prepared by the reaction of an enol ether of the formula (III):

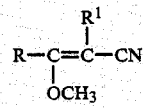

wherein R and $R^1$ are as defined hereinbefore, with hydroxylamine, hydroxylamine hydrochloride, hydroxylamine sulfate, hydroxyurea, etc.

Preferably, this reaction is carried out in a solvent such as water, methanol, ethanol or ethylene glycol, neutralized with an alkali such as sodium methylate or sodium ethylate as necessary, at 60°–120° C. and then with the addition of 5–36% hydrochloric acid (1–2 eq.) at 60°–120° C.

(c) They can be prepared by the reaction of an amidoxime of the formula (IV):

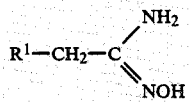

wherein $R^1$ is as defined hereinbefore, with a carboxylic acid ester of the formula (V):

$$RCO_2R^3 \qquad (V)$$

wherein R is as defined hereinbefore and $R^3$ is alkyl.

Preferably, this reaction is carried out in the presence of lithium diisopropylamide in a solvent such as tetrahydrofuran or ethylether at −78°–0° C. and then with the addition of 5–36% hydrochloric acid (6–20 eq.) at 30°–60° C.

(d) They can be prepared by a hydrolysis of the compound of the formula (VI):

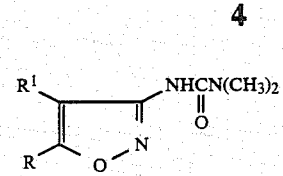

wherein R and $R^1$ are as defined hereinbefore.

Preferably, this reaction is carried out with the addition of 18–36% hydrochloric acid (1.2–10 eq.) in a solvent such as methanol, ethanol, n-propanol or ethylene glycol, preferably in 1 l of ethylene glycol to 1 mole of the compound (I), at 60°–120° C. (e) They can be prepared by a decomposition of the compound of the formula (VI) by the use of a phthalic anhydride and hydrazine hydrate in the usual way.

(f) It can be prepared by the decomposition of the compound of the formula (VII):

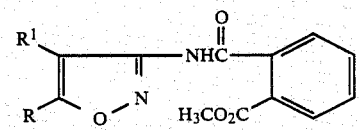

wherein R and $R^1$ are as defined hereinbefore, by the use of hydrazine hydrate in the usual way.

(g) They can be prepared by a hydrolysis of the compound of the formula (VIII):

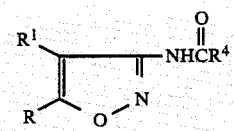

wherein R and $R^1$ are as defined hereinbefore and $R^4$ is alkyl or phenyl. Preferably, this reaction is carried out with the addition of 18–36% hydrochloric acid (1.2–10 eq.) in a solvent such as methanol, ethanol, n-propanol or ethylene glycol, preferably in 1 l of ethylene glycol to 1 mole of the compound (VIII), at 60°–120° C.

Preferably, the processes of preparation described above may be selected suitably deending upon to a particular substituted position of R and a kind of $R^1$. For example, the compounds of (1), (5), (19), (23), (24) and (25) described above are preferably prepared by the procedure of (d)–(g), the compound of (3) is prepared by the procedure of (b). Advantageously, for example, the compound of (21) and the compound wherein R is located at 3-position of isoxazole ring are prepared by the procedure of (a).

The compound of the present invention, wherein $R^1$ is halogen, can be prepared by halogenation of the compound of the formula (I), wherein $R^1$ is hydrogen, in the usual way.

In the compound of the formula (II) being used as the starting material for the preparation of the compound of the formula (I), the compound, wherein $R^1$ is hydrogen or alkyl, is a novel compound. For example, it can be prepared by the condensation reaction of the compound of the formula (V) with the compound of the formula (IX):

$$R^1CH_2CN \qquad (IX)$$

wherein $R^1$ is as defined hereinbefore, in the presence of lithium diisopropylamide in tetrahydrofuran. Preferably, the condensation reaction is carried out in a solvent such as tetrahydrofuran or diethyl ether at −78°–0° C.

The compound wherein $R^1$ is phenyl or substituted phenyl, can be prepared by known methods, for example, the method described in W.R. Nes and A. Barger, J. Am. Chem. Soc., 72, 5409 (1950).

The compound of the formula (III) can be prepared by methylation of the compound of the formula (II) with diazomethane in the usual way.

The compound of the formula (IV) can be prepared by known methods, for example, the method described in F. Eloy and R. Lenaers, Chem. Reviews, 62, 155 (1962).

The compound of the formula (V) is known or can be prepared by known methods.

The compound of the formula (VI) is a novel compound and can be prepared from a compound of the formula (X):

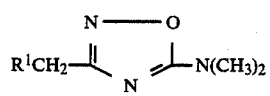 (X)

wherein $R^1$ is as defined hereinbefore, by known methods, for example, the method described in Japanese Patent Laid Open Publication No. 57-175175, which is equivalent to EP 61,882, via the compounds of the formula (XI) and (XII):

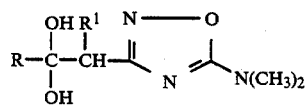 (XI)

and

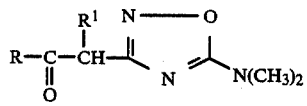 (XII)

wherein R and $R^1$ are as defined hereinbefore. The compounds (XI) and (XII) are also novel.

The compounds of the formula (X) can be prepared by known methods, for example, the reaction of the compound of the formula:

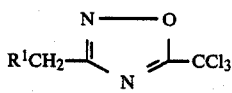

prepared by the method in U.S. Pat. No. 3,227,725 and 3,264,318, with dimethylamine.

The compound of the formula (VIII) can also be prepared by the method described in U.S. Pat. Nos. 3,227,725 and 3,264,318 and Japanese Patent Laid Open Publication No. 57-175175.

The compound of the formula (VII) can be prepared by the reaction of a compound of the formula:

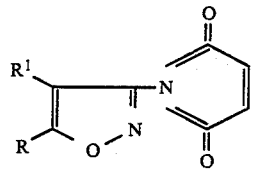

wherein R and $R^1$ are as defined hereinbefore, prepared by the reaction of the compound of the formula (VI) with phthalic anhydride in the usual way, with methanol by known The compounds of the formula (I) of the present invention thus obtained are useful as intermediates for synthesizing such materials as herbicides, fungicides and bactericides and various medicines, in particular, herbicides and fungicides.

The following preparations and examples further illustrate the present invention in detail but are not to be construed to limit the scope thereof.

PREPARATION 1

Trifluoroacetoacetonitirle

A solution of n-butyllithium in n-hexane (280 ml, 0.44 mole) was added to dry diisopropylamine (64 ml, 0.46 mole) dissolved in dry tetrahydrofuran (400 ml), while keeping below 0° C. After being stirred at 0° C. for 30 minutes, the solution was cooled below −72° C. A solution of methyl trifluoroacetate (25.61 g, 0.200 mole), acetonitrile (16.42 g, 0.40 mole) and dry tetrahydrofuran (200 ml) were added dropwise, while keeping below −72° C., and the solution, being kept at −75° C. for additional 45 minutes, was warmed to room temperature over 1 hour. Ice-water (700 ml) was added to the solution and tetrahydrofuran and n-hexane were then evaporated under reduced pressure in a water bath at 40° C. The resulting residue was extracted with diethyl ether to remove neutral and basic components, adjusted to pH 1 with 36% HCl and then extracted with methylene chloride to remove by-products such as acetoacetonitrile. The solution was extracted with diethyl ether. After the extract was dried with anhydrous sodium sulfate, p-toluenesulfonic acid (40 mg, 0.0002 mole) was added to the extract. The extract was distilled at atmospheric pressure and then distilled under reduced pressure to give 26.82 g (crude yield 97.8%) of a crude product. This product was further distilled under reduced pressure to give 16.78 g (61.2%) of the title compound, b.p. 37° C./2.4 mmHg–43° C./2.5 mmHg. The resulting compound was dissolved in $d^6$-acetone to measured NMR, the ratio of the keto form/the enol form was found to be 17/83.

PREPARATION 2

Pentafluropropionylacetonitrile

Acetonitrile (4.1 g, 0.10 mole), ethyl pentafluoropropionate (9.61 g, 0.05 mole) and a solution of n-butyllithium in n-hexane (70 ml, 0.11 mole) were reacted as the procedure illustrated in the preceding Preparation 1 to give 7.28 g (77.8%) of the title compound. The resulting compound was dissolved in $CDCl_3$ to measure NMR, the ratio of the keto form/the enol form was found to be 26/74, m.p. 47°–54° C. (deliquescence), b.p. 69°–71° C./18 mmHg.

Anal. Calcd. for $C_5H_2NOF_5$ $1/7H_2O$: C, 31.66; H, 1.22; N, 7.39. Found: C, 31.65, H, 1.59; N, 7.23.

PREPARATION 3

2-(Trifluoroaceto)propionitrile (a) Propionitrile (19.8 g, 0.36 mole), methyl trifluoroacetate (23.05 g, 0.18 mole) and a solution of n-butyllithium in n-hexane (252 ml, 0.396 mole) were reacted as the procedure illustrated in the preceding Preparation 1 to give 27.72 g (100%) of the title compound. The resulting compound was dissolved in CDCl$_3$ to measure NMR, the ratio of the keto form/the enol form was found to be 49/51, b.p. 52°–57° C./2.7 mmHg.

(b) The title compound was obtained according to the same procedure as in (a) except that methyl trifluoroacetate was replaced with t-butyl trifluoroacetate.
Yield: 14.70 g (54.1%).

PREPARATION 4

2-(Pentafluropropionyl)propionitrile

Propionitrile (13.2 g, 0.24 mole), ethyl pentafluoropropionate (23.05 g, 0.12 mole) and a solution of n-butyllithium in n-hexane (168 ml, 0.264 mole) were reacted as the procedure illustrated in the preceding Preparation 1 to give 22.72 g (crude yield 94.1%) of the crude title compound. The yield calculated as the pure product was 84.1%. The resulting compound was dissolved in CDCl$_3$ to measure NMR, the ratio of the keto form/the enol form was found to be 71/29, b.p. 63°–65° C./28 mmHg.

Anal. Calcd. for C$_6$H$_4$NOF$_5$: C, 35.83; H, 2.01; N, 6.97. Found: C, 35.10; H, 2.52; N, 7.21.

EXAMPLE 1

5-Trifluoromethyl-4-methyl-3-aminoisoxazole

A 8% solution of sodium bicarbonate (288 ml, 0.27 mole, 1.5 eq.) was added to 96% hydroxylamine hydrochloride (19.54 g, 0.27 mole, 1.5 eq.) dissolved in water (180 ml), with stirring below 10° C., to form free hydroxylamine and then crude 2-(trifluoroaceto)propionitrile (27.72 g, 0.18 mole) obtained from Preparation 3 (a) was added to this mixture (pH of the reaction mixture became 6.2). After heating under reflux for 8 hours, 36% hydrochloric acid (15.3 ml, 0.178 mole, 1.0 eq.) was added and the mixture was heated under reflux to react for an additional hour (to cyclize the oxime compound). After completion of the reaction, 48% solution of sodium hydroxide was added dropwise to be adjust above pH 10 while cooling and the solution was extracted witn methylene chloride. After the extract was dried with anhydrous sodium sulfate, methylene chloride was evaporated and the resulting residue was purified by column chromatography on silica gel (Lobar column) to give 9.49 g (31.7%) of the title compound as colorless crystals, m.p. 34.5°–36.0° C., b.p. 67°–70° C./0.78 mmHg.

Anal. Calcd. for C$_5$H$_5$N$_2$OF$_3$: C, 36.15; H, 3.04; N, 16.87. Found: C, 36.20; H, 3.10; N, 16.84.

The structure of this product was also comfirmed by IR, NMR and UV.

3-Trifluoromethyl-4-methyl-5-aminoisoxazole was also obtained. Yield: 0.79 g (2.6%), b.p. 85°–87° C./12 mmHg.

EXAMPLE 2

5-Trifluoromethyl-3-aminoisoxazole

In water (15 ml) was dissolved 96% hydroxylamine hydrochloride (1.63 g, 0.0225 mole, 1.5 eq.). A 8% solution of sodium bicarbonate (24 ml, 0.0225 mole, 1.5 eq.) was added to the solution with stirring below 10° C. to form free hydroxylamine. Crude trifluoroacetoacetonitrile (2.16 g, 0.015 mole) was then added to this mixture and the mixture was heatedunder reflux for 2.5 hours. After the addition of 36% hydrochloric acid (5.7 ml), the mixture was heated under reflux to react for an additional hour. After completion of the reaction, a 48% solution of sodium hydroxide was added dropwise to be adjust above pH 10 while cooling and the solution was extracted with methylene chloride. After the extract was dried with anhydrous sodium sulfate, methylene chloride was evaporated and the resulting residue was purified by column chromatography on silica gel (Lobar column) to give the mixture (0.60 g, 26.0%) of the title compound and 3-trifluoromethyl-5-aminoisoxazole (the ratio of both by NMR measurement was 4.9:95.6).

EXAMPLE 3

5-Pentafluoroethyl-3-aminoisoxazole

The title compound was obtained according to the same procedure as described in Example 1 except that crude pentafluoropropionylacetonitrile (2.20 g, 0.010 mole) and water (10 ml) were used. Yield: 0.0104 g (0.5%). 3-Pentafluoroethyl-5-aminoisoxazole was also obtained.

Yield: 0.025 g (1.2%).

EXAMPLE 4

5-Pentafluoroethyl-4-methyl-3-aminoisoxazole

The title compound was obtained as colorless crystals according to the same procedure as described in Example 1 except that 2-(pentafluropropionyl)propionitrile (25.11 g, 0.12 mole), water (120 ml) and 36% hydrochloric acid (10.2 ml) were used. Yield: 9.04 g (34.9%), m.p. 32°–34° C., b.p. 86°–87° C./2.7 mmHg.

Anal. Calcd. for C$_6$H$_5$N$_2$OF$_5$: C, 33.34; H, 2.34; N, 12.96. Found: C, 33.09; H, 2.54; N, 13.06.

3-Pentafluoroethyl-4-methyl-5-aminoisoxazole was also obtained. Yiled: 0.96 g (3.7%).

EXAMPLE 5

5-Trifluoromethyl-3-aminoisoxazole

Dry methanol (220 ml) and 96% hydroxylmine hydrochloride (11.52 g, 0.159 mole) were added to trifluoroacetoacetonitrile (16.78 g, 0.122 mole) and the mixture was heated under reflux with stirring for 68 hours. Methanol was then evaporated under reduced pressure and after the addition of water (240 ml) a 48% solution of sodium hydroxide was added to the resulting residue to be adjust above pH 11. The solution was extracted with methylene chloride and after the extract being dried with anhydrous soidum sulfate, the solvent was evaporated under reduced pressure to give the title compound (10.30 g, 55.2%) as little colored crystals, m.p. 57°–58° C., b.p. 66°–67° C./0.8 mmHg.

EXAMPLE 6

3-Pentafluoroethyl-5-aminoisoxazole

The title compound was obtained as colorless plates according to the same procedure as described in Example 5 except pentafluoropropionylacetonitrile (2.85 g, 0.015 mole) was used. Yield: 2.31 g (76.2%), m.p. 86°–87° C., b.p. 89°–90° C./3 mmHg.

EXAMPLE 7

3-Trifluoromethyl-4-methyl-5-aminoisoxazole

The title compound was obtained according to the same procedure as described in Example 5 except that α-(trifluoroaceto)propionitrile (4.53 g, 0.030 mole) was used. Yield: 4.55 g (83.3%), m.p. 53°–54° C., b.p. 65°–67° C./0.75 mmHg.

Anal. Calcd. for $C_5H_5N_2OF_3$: C, 36.15; H, 3.04; N, 16.87. Found: C, 36.12; H, 3.10; N, 16.98.

EXAMPLE 8

3-Pentafluoroethyl-4-methyl-5-aminoisoxazole

The title compound was obtained as colorless needles according to the same procedure as described in Example 5 except that 2-(pentafluoropropionyl)propionitrile (2.01 g, 0.010 mole) was used. Yield: 1.85 g (86.5%), m.p. 49°–51° C., b.p. 94°–95° C./5 mmHg.

EXAMPLE 9

3-Trifluoromethyl-5-aminoisoxazole (a) Trifluoroacetoacetonitrile (1.37 g, 0.010 mole), hydroxylamine hydrochloride (1.04 g, 0.015 mole) and a 8% solution of sodium bicarbonate (15.75 g, 0.015 mole) were heated under reflux for 2.5 hours. After the addition of 36% hydrochloric acid (1.01 g, 0.010 mole), the mixture was heated under reflux for an additional hour to give a product (1.2 g, 78%). According to the measurement of NMR, it was found that this compound contained 94% of the title compound and 6% of 5-trifluoromethyl-3-aminoisoxazole.

(b) Trifluoroacetoacetonitrile (1.37 g, 0.010 mole), hydroxylamine hydrochloride (0.69 g, 0.010 mole), ethanol and water were heated under reflux for 3 hours. After the addition of hydrochloric acid (1.21 g, 0.012 mole), the mixture was further heated under reflux to give the title compound (0.21 g, 13.7%).

(c) Trifluoroacetoacetonitrile (5.12 g, 0.030 mole), hydroxyurea (2.51 g, 0.033 mole) and methanol were heated under reflux for 150 hours to give the title compound (0.50 g, 11.0%).

EXAMPLE 10

3-Trifluoromethyl-5-aminoisoxazole

A 15% solution of n-butyllithium in n-hexane (500 ml) was added to diisopropylamine (116.5 ml) dissolved in dry tetrahydrofuran (720 ml), keeping below 0° C. After being stirred at 0° C. for 30 minutes, the solution was cooled below −72° C. A solution of methyl trifluoroacetate (46.28 g, 0.3614 mole), acetonitrile (29.67 g) and dry tetrahydrofuran (300 ml) were added dropwise, keeping below −72° C., and the solution, after being kept at −75° C. for additional 45 minutes, was warmed to room temperature over 1 hour. Ice-water (360 ml) was added to the solution and tetrahydrofuran and n-hexane were then evaporated under reduced pressure in a water bath at 40° C. The resulting residue was extracted with diethylether to remove neutral and basic components. It was adjusted to pH 1 with 36% HCl and then extracted with methylene chloride to remove by-products such as acetoacetonitrile. The solution was extracted with diethyl ether. p-Toluenesulfonic acid (0.07 g, 0.0003614 mole) was added to the extract and diethyl ether was distilled off at atmospheric pressure (in a water bath at 60° C.) by using a distillation apparatus equipped with a fractionating column. The resulting residue was distilled under reduced pressure at room temperature to give a crude product (56.44 g, 114%). Methanol (651 ml) and 97% hydroxylamine hydrochloride (33.66 g, 0.4698 mole) were added to this product and the mixture was heated under reflux for 68 hours. Methanol was distilled off under reduced pressure and ice-water (240 ml) was added to the resulting residue. This was adjusted above pH 11 with a 48% solution of sodium hydroxide and after being extracted with methylene chloride, the solvent was evaporated. The resulting residue was then distilled under reduced pressure to give the title compound (34.13 g, 62.1%) as pale red crystals, b.p. 85°–88° C./3.5 mmHg. This compound was recrystallized from benzene-cyclohexane to give colorless plates, m.p. 57°–58° C. The structure of this compound was confirmed by IR, NMR, UV and elemental analysis.

EXAMPLE 11

3-Pentafluoroethyl-5-aminoisoxazole

The title compound was obtained according to the same procedure as described in Example 10 except that ethyl pentafluoropropionate (13.45 g, 0.07 mole) was used. Yield: 9.44 g (66.7%).

EXAMPLE 12

3-Trifluoromethyl-4-methyl-5-aminoisoxazole

The title compound was obtained according to the same procedure as described in Example 10 except that methyl trifluoroacetate (10.24 g, 0.08 mole) was used. Yield: 7.89 g (59.4%).

EXAMPLE 13

3-Pentafluoroethyl-4-methyl-5-aminoisoxazole

The title compound was obtained according to the same procedure as described in Example 10 except that ethyl pentafluoropropionate (23.05 g, 0.12 mole) was used. Yield: 19.39 g (74.7%).

PREPARATION 5

α-Trifluoroacetyl-p-fluorophenylacetonitrile

Dry ethanol (15 ml) was added to sodium metal (1.22 g, 0.0530 mole) and the mixture was heated under reflux to dissolve sodium metal perfectly. A mixture of ethyl trifluoroacetate (7.53 g, 0.0530 mole) and p-fluorophenylacetonitrile (6.76 g, 0.0500 mole) was added dropwise over 30 minutes. The mixture, after being heated under reflux for 10 hours, was extracted with methylene chloride to remove neutral and basic components. To the mixture was then added 36% hydrochloric acid to adjust below pH 2 and the mixture was extracted with diethyl ether again. After being dried, the solvent was distilled off under reduced pressure to give the crude title compound (10.47 g, 84.0%). The product showed a single spot on thin-layer chromatography. The product was recrystallized from benzenecyclohexane to recover the monohydrate of the title compound (8.97 g, 77.0%) as pale yellow prisms. The structure of this compound was confirmed by IR and NMR.

PREPARATION 6

α-(Trifluoroacetyl)phenylacetonitirle

The title compound was obtained according to the same procedure as described in Preparation 5 except that ethyl trifluoroacetate (50.00 g, 0.352 mole) was used. Yield: 70.45 g (92.3%), m.p. 85°–87° C. This compound was dissolved in $CDCl_3$ to measure NMR, the ratio of the enol form was found to be 100%. This product was recrystallized from benzene-cyclohexane to give the monohydrate of the title compound as colorless needles, m.p. 87°–88° C. [see Nes et al., J. Am. Chem. Soc., 72, 5409 (1950).].

PREPARATION 7

α-(Pentafluoropropionyl)phenylacetonitrile

The title compound was obtained according to the same procedure as described in Preparation 5 except that ethyl pentafluoropropionate (24.44 g, 0.127 g) was used. Yield: 19.41 g (61.5%), m.p. 94°–95° C.

This compound was dissolved in CDCl₃ to measure NMR, the ratio of the keto form/the enol form was found to be 38/62.

Anal. Calcd. for $C_{11}H_6NOF_5$: C, 50.20; H, 2.30; N, 5.32. Found: C, 50.48; H, 2.50; N, 5.36.

PREPARATIONS 8 TO 14

The following compounds were prepared according to the same procedure as described in Preparation 5. The results are shown in Table 1.

In the table, the second column shows kinds and positions of one or more substituents on benzene ring of the formula (A):

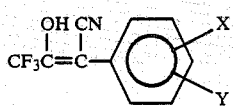
(A)

and the third column shows the amount of the compound of the formula (B):

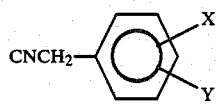
(B)

EXAMPLE 14

3-Trifluoromethyl-4-phenyl-5-aminoisoxazole (a) Methanol (53 ml) and 96% hydroxylamine hydrochloride (2.82 g, 0.0390 mole, 1.3 eq.) were added to -(trifluoroacetyl)phenylacetonitrile (6.96 g, 0.0300 mole) and the mixture was heated under reflux for 68 hours. After methanol was distilled off under reduced pressure and the resulting residue was neutralized with a 8% solution of sodium bicarbonate, the solution was extracted with methylene chloride. After being dried with anhydrous sodium sulfate, it was concentrated and purified by column chromatography on silica gel to give the title compound (5.62 g, 82.1%). The product was recrystallized from benzene-cyclohexane to recover the title compound (4.80 g, 70.1%) as pale yellow needles, m.p. 89°–91° C.

(b) The mixture of the title compound (82.9%) and 5-trifluoromethyl-4-phenyl-3-aminoisoxazole (4.8%) was obtained according to the same procedure as described in Example 5 except that -(trifluoroacetyl)-phenylacetonitrile (2.13 g, 0.010 mole) was used.

EXAMPLES 15 TO 21

The following compounds were prepared according to the same procedure as described in Example 14 (a). The results are shown in Table 2.

In the table, the second column shows kinds and positions of one or more substituents on benzene rings of compounds of the formula (B) and (C):

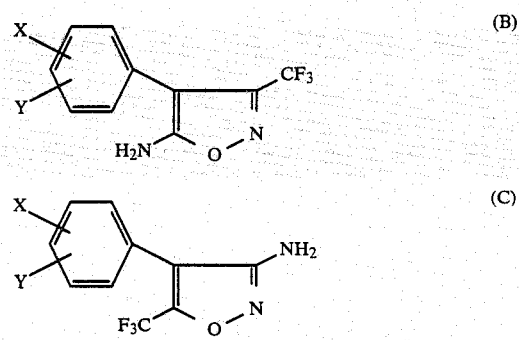

The third column shows the yield of the compound purified by column chromatography on silica gel and the fourth column shows the ratio by weight of the compound of the formula (B) and (C) measured by HPLC.

TABLE 1

| Prep. No. | Substituent | Starting material g (mole) | Ethanol (ml) | Crude yield g (%) | Crystal form | Recrystallization solvent | m.p. (°C.) |
|---|---|---|---|---|---|---|---|
| 8 | 4-CH₃ | 26.23 (0.20) | 60 | 45.92 (99.1) | pale yellow needles (¼ hydrate) | benzene-cyclohexane | 59.5–60.5 |
| 9 | 4-Cl | 30.94 (0.20) | 60 | 45.11 (84.9) | slight yellow needles (1 hydrate) | benzene-cyclohexane | 90.0–91.0 |
| 10 | 4-OCH₃ | 30.35 (0.20) | 60 | 50.83 (104.5) | pale yellow crystals (deliquescence) | — | 77.0–79.5 |
| 11 | 2-Cl,4-Cl | 9.49 (0.05) | 20 | 4.96 (35.2) | slight yellow crystals (deliquescence) | — | 121.0–122.5 |
| 12 | 2-Cl,6-Cl | 9.49 (0.05) | 17 | 1.70 (12.1) | colorless needles | benzene-cyclohexane | 184–185 (dec.) |
| 13 | 3-OCH₃,4-OCH₃ | 35.44 (0.20) | 60 | 51.85 (94.9) | pale brown crystals (deliquescence) | — | 145–146.5 |
| 14 | 3,4-OCH₂O— | 29.75 (0.1846) | 55 | 46.09 (97.1) | pale brown crystals (deliquescence) | — | 111–113 |

TABLE 2

| Ex. No. | Substituent | Yield (%) | Content ratio (B)/(C) by weight |
|---|---|---|---|
| 15 | unsubstituted | 86.3 | 94.5/5.5 |
| 16 | 4-F | 85.3 | 93.8/6.2 |
| 17 | 4-Cl | 65.1 | 87.2/12.8 |
| 18 | 4-CH₃ | 80.7 | 95.6/4.4 |
| 19 | 4-OCH₃ | 84.9 | 94.9/5.1 |
| 20 | 3-OCH₃ 4-OCH₃ | 85.0 | 96.1/3.9 |
| 21 | 3,4-OCH₂O | 84.6 | 95.1/4.9 |

The physical properties of the resulting compounds are shown in Table 3.

In the table, the first column identifies the compounds by the number of the preparative example and the formula (B) or (C), and the fifth column shows the values of λ max and ε measured in 95% ethanol.

TABLE 3

| Comp. | Crystal form | Recrystallization solvent | m.p. (°C.) | UV absorption (nm(× 10³)) | Elemental analysis (calcd./found) C | H | N |
| --- | --- | --- | --- | --- | --- | --- | --- |
| 15(B) | slight yellow needles | benzene-cyclohexane | 89.0–91.0 | 200.5(13.1) 259(12.6) | 52.63 52.75 | 3.10 3.18 | 12.28 12.18 |
| 15(C) | colorless needles | cyclohexane | 92.0–93.0 | 199.5(21.2) 230(5.63) 257(4.62) | 52.63 52.56 | 3.10 3.21 | 12.28 12.31 |
| 16(B) | slight yellow needles | benzene-cyclohexane | 98.0–99.0 | 203(12.3) 258(11.0) | 48.79 48.59 | 2.46 2.63 | 11.38 11.54 |
| 16(C) | colorless needles | n-hexane | 91.0–92.0 | — | — | | |
| 17(B) | colorless prisms | benzene-cyclohexane | 139.0–141.0 | 199(17.0) 263(13.9) | 45.73 45.70 | 2.31 2.63 | 10.67 10.60 |
| 17(C) | colorless needles | n-hexane | 114.5–115.5 | — | — | | |
| 18(B) | colorless needles | benzene-cyclohexane | 131–132 | 199.5(13.5) 259(12.4) | 54.54 54.97 | 3.75 3.38 | 11.57 11.63 |
| 18(C) | colorless needles | n-hexane | 88.5–89.5 | — | — | | |
| 19(B) | colorless needles | benzene-cyclohexane | 126.0–127.0 | 199(24.5) 255(13.1) | 51.16 51.27 | 3.52 3.44 | 10.85 10.92 |
| 19(C) | pale yellow columns | n-hexane | 87.0–88.0 | — | — | | |
| 20(B) | slight yellow plates | ethyl acetate-cyclohexane | 138.5–139.5 | 200(38.2) 258(12.5) | 50.00 49.91 | 3.85 3.75 | 9.72 9.77 |
| 20(C) | pale yellow prisms | ethyl acetate-n-hexane | 130.5–131.5 | — | — | | |
| 21(B) | slight brown needles | benzene-cyclohexane | 164.0–165.0 | 200.5(35.2) 261(11.1) | 48.53 48.56 | 2.60 2.77 | 10.29 10.28 |
| 21(C) | pale yellow prisms | ethyl acetate-n-hexane | 130.5–131.5 | — | — | | |

EXAMPLE 22

3-Pentafluoroethyl-4-phenyl-5-aminoisoxazole

The title compound was obtained as colorless needles according to the same procedure as described in Example 5 except that α-(pentafluoropropionyl)-phenylacetonitrile (13.61 g, 0.050 mole) was used. Yield: 0.97 g (7.0%), m.p. 79°–80° C.

Anal. Calcd. for $C_{11}H_7N_2OF_5$: C, 47.49; H, 2.54; N, 10.07. Found: C, 47.49; H, 2.80; N, 10.20.

5-Pentafluoroethyl-4-phenyl-3-aminoisoxazole (0.47 g, 3.4%) was also obtained. Yield: 0.47 g (3.4%).

EXAMPLE 23

5-Trifluoromethyl-4-phenyl-3-aminoisoxazole

A crude product was obtained according to the same procedure as described in Example 1 except that α-(trifluoroacetyl)phenylacetonitrile (23.12 g, 0.10 mole) was used. Crude yield: 3.69 g (16.2%). According to the measurement of NMR, it was found that this compound contained 83.2% of the title compound and 11.8% of 3-trifluoromethyl-4-phenyl-5-aminoisoxazole. The crude product was purified by column chromatography on silica gel as described in Example 1 to give the title compound (3.06 g, 13.4%) as colorless crystals, m.p. 91.5°–92.0° C.

EXAMPLE 24:

3-Pentafluoroethyl-4-phenyl-5-aminoisoxazole

Using α-(pentafluoropropionyl)phenylacetonitrile (2.65 g, 0.010 mole) as the procedure described in Example 1 gave the title compound (0.16 g, 0.6%) as colorless prisms, m.p. 83°–84° C.

EXAMPLE 25

5-Trifluoromethyl-4-phenyl-3-aminoisoxazole

Water (170 ml) was added to 96% hydroxylamine hydrochloride (2.17 g, 0.0300 mole, 1.5 eq.). The solution was neutralized with a 8% solution of sodium bicarbonate (31.5 g, 0.0300 mole, 1.5 eq.), while keeping below 10° C. To this was added -(trifluroacetyl)-phenylacetonitrile (4.62 g, 0.0200 mole) and the mixture was heat under reflux for 8 hours. After 36% hydrochloric acid (1.7 ml, 0.0200 mole) being added, the mixture was heated under reflux for an additional hour. A 8% solution of sodium bicarbonate was then added to neutralize and the solution was extracted with methylene chloride. After the extract was dried with anhydrous sodium sulfate, it was concentrated and purified by column chromatography on silica gel to give 0.7 g of the product. According to the measurement of HPLC, it was found that this product contained 83.3% of the title compound and 16.7% of 3-trifluoromethyl-4-phenyl-5-aminoisoxazole.

PREPARATION 15

3-Methoxy-3-(trifluoromethyl)acrylonitrile

Diethylether (300 ml) was added to trifluoroacetoacetonitrile (13.7 g, 0.100 mole) and to this was added an ethereal solution of diazomethane, which was prepared from N-nitrosomethylurea (25.77 g, 0.250 mole), a 50% solution of potassium hydroxide (112.22 g, 1.00 mole) and diethylether (180 ml), with ice cooling. The solution was allowed to stand over night while cooling with ice. Next day, until the pH being 3–4 (by an universal test paper) acetic acid in limited amounts was added to the reaction mixture to decompose an excess of diazomethane and the solution was concentrated to about 200 ml at atmospheric pressure by using a distillation apparatus equipped with a fractionating column. The concentrate was washed with a 8% solution of sodium bicarbonate and water and dried with anhydrous sodium sulfate. Diethyl ether was distilled off by using a distillation apparatus equipped with a fractionating column at atmospheric pressure and the residue was distilled under reduced pressure to give the title compound (5.31 g, 35.1%) as a colorless liquid, b.p.

58.0° C./68 mmHg–64.0° C./70.0 mmHg. The structure of the product was confirmed by IR and NMR.

PREPARATION 16

3-Methoxy-3-(pentafluoroethyl)acrylonitrile

The title compound was obtained as a colorless liquid according to the same procedure as described in Preparation 15 except that pentafluoropropionylacetonitrile (18.7 g, 0.100 mole) was used. Yield: 13.63 g (67.8%), b.p. 65°–69° C./69 mmHg. The structure of the product was confirmed by NMR.

PREPARATION 17

3-Methoxy-3-(trifluoromethyl)methacrylonitrile

The title compound was obtained as a colorless liquid according to the same procedure as described in Preparation 15 except that 2-(trifluoroaceto)propionitrile (15.11 g, 0.100 mole) was used. Yield: 11.4 g (69.6%), m.p. 68°–76.5° C./28 mmHg. It was found that the title compound was the mixture of the E- and the Z-form by the measurement of NMR. The ratio of both was 20/80 but no assignment was made.

PREPARATION 18

3-Methoxy-3-(pentafluoroethyl)methacrylonitrile

The title compound was obtained as a colorless liquid (2.31 g) from the forerun and a pale brown liquid (6.66 g) from the main distillate of the vacuum distillation according to the same procedure as described in Preparation 15 except that 2-(pentafluoropropionyl)propionitrile was used. Each fraction was a mixture of the E- and the Z-form, 37/63 and 3/97, respectively (no assignment).

The boiling point of the forerun is 85°–89° C./48 mmHg and that of the main distillate is 80°–86° C./28 mmHg.

PREPARATION 19

3-Methoxy-2-phenyl-3-(trifluoromethyl)-acrylonitrile

The crude title compound was obtained according to the same procedure as described in Preparation 15 except that (trifluoroaceto)phenylacetonitrile (2.13 g, 0.010 mole) was used. This product was employed for a further reaction without additional purificatinn.

PREPARATION 20

3-Methoxy-3-pentafluoroethyl-2-phenylacrylonitrile

The crude title compound was obtained according to the same procedure as described in Preparation 15 except that (pentafluoropropionyl)phenylacetonitrile (0.79 g, 0.003 mole) was used and the reaction was carried out with ice cooling for 30 minutes. This product was employed for a further reaction without additional purification.

EXAMPLE 26

5-Trifluoromethyl-3-aminoisoxazole

Sodium metal (0.48 g, 0.0210 mole, 1.5 eq.) was added to dry methanol (28 ml) and 97% hydroxylamine hydrochloride (1.50 g, 0.0210 mole, 1.5 eq.), obtained from Nakarai Chemicals, was then added to the resulting solution with ice cooling. After being stirred at room temperature for 15 minutes, 3-methoxy-3-(trifluromethyl)acrylonitrile (2.12 g, 0.0140 mole) was added and heated under reflux for 16 hours. To the solution was then added 36% hydrochloric acid (3.54 g, 0.0350 mole, 2.5 eq.) and it was heated under reflux for 1 hour. Methanol was distilled off at atmospheric pressure over 1 hour by using a distillation apparatus equipped with a fractionating column. Water (28 ml) was added to the residue and it was extracted with methylene chloride after pH being adjusted above 11 with 48 sodium hydroxide. The extract was dried with anhydrous sodium sulfate and it was distilled at atmospheric pressure and then under reduced pressure at room temperature by using a distillation apparatus equipped with a fractionating column to give the crude title compound (0.8968 g). This product was purified by column chromatography on silica gel to give the title compound (0.2201 g, 10.3%) and 3-trifluoromethyl-5-aminoisoxazole (0.4738 g, 22.3%).

EXAMPLE 27

3-Amino-5-pentafluoroethylisoxazole

The title compound (0.9571 g, 33.8%) and 3-pentafluoroethyl-5-aminoisoxazole (0.2181 g, 7.7%) were obtained according to the same proceudre as described in Example 26 except that 3-methoxy-3-(pentafluoroethyl)-acrylonitrile (2.82 g, 0.0140 mole) was used.

EXAMPLE 28

5-Trifluoromethyl-4-methyl-3-aminoisoxazole

The title compound (1.4988 g, 64.5%) and 3-trifluoromethyl-4-methyl-5-aminoisoxazole (0.0249 g, 1.1%) were obtained according to the same procedure described in Example 26 except that 3-methoxy-3-(trifluoromethyl)methacrylonitrile (2.31 g, 0.0140 mole) and 36% hydrochloric acid (1.42 g, 0.0140 mole, 1 eq.) were used and reflux was carried out for 68 hours.

EXAMPLE 29

5-Pentafluoroethyl-4-methyl-3-aminoisoxazole

The title compound (0.3497 g, 11.6%) and 3-pentafluoroethyl-4-methyl-5-aminoisxazole (0.0923 g, 3.1 %) were obtained according to the same procedure as described in Example 26 except that 3-methoxy-3-(pentafluroethyl)-methacrylonitrile (3.01 g, 0.0410 mole) was used.

EXAMPLE 30

3-Trifluoromethyl-4-phenyl-5-aminoisoxazole

The title compound was obtained according to the same procedure as described in Example 26 except that 3-methoxy-2-phenyl-3-trifluoromethylacrylonitrile (2.27 g, 0.0100 mole) was used, reflux was carried out for 5 hours and hydrochloric acid was not used. Yield: 0.96 g.

EXAMPLE 31

5-Pentafluoroethyl-4-phenyl-3-aminoisoxazol

The title compound (0.0675 g) and 3-pentafluoroethyl-4-phenyl-5-aminoisoxazole (0.1125 g) were obtained according to the same procedure as described in Example 26 except that 3-methoxy-2-phenyl-3-pentafluoroethylacrylonitrile (8.31 g, 0.030 mole) was used, reflux was carried out for 38 hours and hydrochloric acid was not used.

EXAMPLE 32

5-Trifluoromethyl-4-phenyl-3-aminoisoxazole

Under a nitrogen atmosphere, dry tetrahydrofuran (90 ml) was added to diisopropylamine (14.5 ml, 0.105 mole, 5.23 mole) and then to the solution was added a 15% solution of butyllithium in n-hexane (64 ml, 0.100 mole, 5.0 eq.) with cooling below 0° C. After keeping the mixture at 0° C. for 30 minutes, it was cooled at −75° C. The mixture of t-butyl trifluoroacetate (10.21 g, 0.0600 mole, 3 eq.), phenylacetamide oxime (3.00 g, 0.0200 mole) and dry tetrahydrofuran (45 ml) was added dropwise, keeping the mixture below −72° C. After the mixture was stirred at −75° C. for 1 hour, it was allowed to warm to room temperature over 1 hour. To the mixture was added 10% hydrochloric acid (90 ml, 0.246 mole) and refluxed for 2.5 hours. The reaction mixture was distilled under reduced pressure to remove tetrahydrofuran and n-hexane. The resulting residue was adjusted above pH 13 with a 48% solution of sodium hydroxide and extracted with methylene chloride. After the extract was dried with anhydrous sodium sulfate, the solvent was distilled off. The resulting residue was purified by column chromatography on alumina and silica gel to give the title compound (0.60 g, 13.1%). This product was recrystallized from cyclohexane to give colorless needles, m.p. 92.0°–93.0° C. The structure of this compound was confirmed by IR, NMR and UV.

EXAMPLE 23

5-Pentafluoroethyl-4-phenyl-3-aminoisoxazole

The title compouhd was obtained according to the same procedure as described in Example 32 except that phenylacetoamide oxime (1.50 g, 0.0100 mole) and t-butyl pentafluoropropionate (6.66 g, 0.0300 mole) were used.

Yield: 0.07 g (2.5%).

PREPARATION 21

3-(2,2-Dihydroxy-2-trifluoromethyl)ethyl-5-diethylamino-1,2,4-oxadiazole

Dry diisopropylamine (33.75 g, 0.334 mole) was dissolved in dry tetrahydrofuran (290 ml) and the solution was then cooled to −60° C. A 15% solution of n-butyllithium in n-hexane (200 ml, 0.318 mole) was added to this solution and it was stirred at 0° C. for 30 minutes. A solution of 5-dimethylamino-3-methyl-1,2,4-oxadiazole (18.55 g, 0.145 mole), previously prepared, t-butyl trifluoroacetate (37.00 g, 0.218 mole) and tetrahydrofuran (145 ml) was added dropwise to this reaction solution, being cooled to −75° C. (the temperature was kept below −75° C. during the addition). After being stirred at −75° C. for 1 hour, the cooling bath was removed. When the temperature rose to 0° C., the solution was cooled again to −25° C. and cold 2N hydrochloric acid (346 ml, 0.652 mole) was added to neutralize the solution (the temperature rose to 3° C.). Tetrahydrofuran and n-hexane were evaporated under reduced pressure in a water bath at 30° C. and the resulting residue was extracted with diethyl ether. The extract was evaporated under reduced pressure in a water at 30° C. to give 43.55 g of crystals. This product was recrystallized from benzene to give the title compound as colorless prisms. Yield: 27.75 g, m.p. 84.0°–85.0° C.

NMR (CDCl$_3$, δ): 3.04 (s, 2H, —CH$_2$—), 3.14 (s, 6H, —N(CH$_3$)$_2$), 5.25 (b.s., 2H, —C(OH)$_2$—).

IR (CHCl$_3$, cm$^{-1}$): 3570(OH), 3270 br.*(OH), 1650(C=N) (*br.=broad).

Anal. Calcd. for C$_7$H$_{10}$N$_3$O$_3$F$_3$: C., 34.86; H, 4.18; N, 17.42. Found: C, 34.89; H, 4.16; N, 17.54.

The mother liquor was purified by column chromatography on silica gel and recrystallization from benzene to give 6.11 g of crystals. This product contains the title compound and 3-dimethylcarbamoylamino-5-trifluoromethylisoxazole in the ratio 7:3. Both yields calculated as the pure product were 92.6% and 5.7%, respectively.

PREPARATION 22

5-Dimethylamino-3-(2-hydroxy-2-pentafluroethyl)vinyl-1,2,4-oxadiazole

The title compound was obtained as colorless flakes according to the same procedure as described in Preparation 21 except that 5-dimethylamino-3-methyl-1,2,4-oxadiazole (1.27 g, 0.010 mole) and t-butyl pentafluropropionate (3.3 g, 0.015 mole) were used. Yield calculated as the pure product: 71.1%, m.p. 103.0°–104.0° C. (recrystallization solvent: cyclohexane).

NMR (CDCl$_3$, δ): 3.17 (s, 6H, —N(CH$_3$)$_2$), 5.95 (s, 1H, —CH=).

IR (CHCl$_3$, cm$^{-1}$): 2950$^{br}$ (OH), 1660, 1670, 1680 (C=N).

Anal. Calcd. for C$_8$H$_8$N$_3$O$_2$F$_5$:C, 35.18; H, 2.95; N, 15.38. Found: C, 35.14; H, 3.10; N, 15.49.

3-Dimethylcarbamoylamino-5-pentafluoroethylisoxazole (0.68 g, 24.9%) was also obtained.

PREPARATION 23

5-Dimethylamino-3-(2-hydroxy-2-heptafluoropropyl)-vinyl-1,2,4-oxadiazole

The title compound was obtained as colorless plates according to the same procedure as described in Preparation 21 except that 5-dimethylamino-3-methyl-1,2,4-oxadiazole (2.90 g, 0.028 mole) and t-butyl heptafluorobutyrate (11.34 g, 0.042 mole) were used and purification methods were changed (recrystallization from cyclohexane, column chromatography on silica gel and then recrystallization from dichloroethane-n-hexane). Yield calculated as the pure product: 42.1%, m.p. 81.5°–82.5° C.

NMR (CDCl$_3$, δ): 3.19 (s, 6H, —N(CH$_3$)$_2$), 5.97 (s, 1H, —CH=).

IR (CHCl$_3$, cm$^{-1}$): 2950$^{br.}$ (OH), 1650, 1670 (C=N).

Anal. Calcd. for C$_9$H$_8$N$_3$O$_2$F$_7$: C, 33.45; H, 2.50; N, 13.00. Found: C, 33.23; H, 2.61; N, 13.30. 3-Dimethylcarbamoylamino-5-heptafluorobutylisoxazole (4.225 g, 57.3%) was also obtained.

PREPARATION 24

5-Dimethylamino-3-(3-trifluoromethyl)butyrylmethyl-1,2,4-oxadiazole

The title compound was obtained as pale yellow crystals according to the same procedure as described in Preparation 21 except that 5-dimethylamino-3-methyl-1,2,4-oxadiazole (6.07 g, 0.0477 mole) and methyl 3-trifluoromethylbutyrate (12.17 g, 0.0716 mole) were used and purification methods were changed (silica gel column chromatography and then sublimation). Yield: 0.472 g (3.7 m.p. 46.0°–47.5° C. NMR (CDCl$_3$, ): 1.11 (d, 3H,

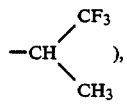

3.12 (s, 6H, —N(CH$_3$)$_2$), 3.63 (s, 2H, —COCH$_2$—), 2.5–3.0 (m, 3H,

IR (CCl$_4$, cm$^{-1}$): 1640 (C=N), 1730 (C=O). Anal. Calcd. for C$_{10}$H$_{14}$N$_3$O$_2$F$_3$: C, 45.28; H, 5.32; N, 15.84. Found: C, 45.16; H, 5.30; N, 15.77. 3-Dimethylcarbmoylamino-5-(2-trifluoromethyl)isopropylisoxazole (1.11 g, 8.8%) was also obtained.

PREPARATION 25

3-Dimethylcarbamoylamino-5-trifluoromethylisoxazole

After 3-(2,2-dihydroxy-2-trifluoromethyl)ethyl-5-dimethylamino-1,2,4-oxadiazole (19.42 g, 0.08052 mole) was heated with stirring at 90° C. for 1.5 hours, the product was dried under reduced pressure to give the crude title compound (18.24 g, crude yield 101.5%) as colorless prisms, m.p. 126.0°–126.5° C.

PREPARATIONS 26 TO 28

According to the same procedure as described in Preparation 25, the following compounds were prepared. The results are shown in Table 4.

TABLE 4

| Prep. No. | Starting material g (mole) | Rearrangement condition | Product | Crude yield g (%) | Crystal form m.p. (°C.) |
|---|---|---|---|---|---|
| 26 | 5-dimethylamino-3-pentafluoropropionyl-methyl-1,2,4-oxadiazole 0.8195 (0.003) | ethanol 80° C. 0.5 h | 3-dimethylcarbamoyl-amino-5-pentafluoro-ethylisoxazole | 0.8254 (100.7) | pale yellow prisms 93.5–94.5 |
| 27 | 5-dimethylamino-3-heptafluorobutyryl-methyl-1,2,4-oxadiazole 0.646 (0.002) | ethanol 60° C. 0.5 h | 3-dimethylcarbamoyl-amino-5-heptafluoro-butylisoxazole | 0.645 (99.8) | slight yellow prisms 94.5–95.5 |
| 28 | 5-dimethylamino-3-(3-trifluoromethyl)-butyrylmethyl-1,2,4-oxadiazole 0.42 (0.0016) | KOH/ethanol room temp. 6.5 h | 3-dimethylcarbamoyl-amino-5-(2-trifluoro-methyl) butylisoxazole | 0.410 (98) | colorless flakes 143.0–143.3 |

PREPARATION 29

3-Dimethylcarbamoylamino-5-trifluoromethylisoxazole

Dry tetrahydrofuran (84.6 ml) was added to diisopropylamine (dried with potassium hydroxide, 9.85 g, 0.0973 mole) nder a nitrogen atmosphere. The solution was cooled to −60° C. and thereto was added a 15% solution of n-butyllithium in n-hexane (58.5 ml, 0.0901 mole). After being stirred at 0° C. for 30 minutes, it was cooled to −75° C. A mixture of t-butyl trifluoroacetate (10.80 g, 0.0635 mole), 5-dimethylamino-3-methyl-1,2,4-oxadiazole (5.72 g, 0.0423 mole) and dry tetrahydrofuran (423 ml) was added dropwise to it at −73−−75° C. over 1.5 hours. After being stirred at −75° C. for 1 hour, it was allowed to warm to room temperature over 1 hour. It was further heated to 50° C. and stirred for 30 minutes. 1N hydrochloric acid (190 ml) was then added thereto with ice cooling and tetrahydrofuran and n-hexane were distilled off under reudced pressure in a water bath at 40° C. After being extracted with methylene chloride, the extract was concentrated and purified column chromatrography on silica gel to give the crude title compound (8.91 g, crude yield 94.4%). Repeated recrystallizations from benzene gave colorless fine needles, m.p. 126.0°–126.5° C. The structure of this compound was confirmed by IR, NMR and elemental analysis.

Anal. Calcd. for C$_7$H$_8$N$_3$C$_2$F$_3$: C, 37.68; H, 3.61; N, 18.83. Found: C, 37.49; H, 3.62; N, 18.76.

PREPARATION 30

3-Dimethylcarbamoylamino-5-trifluoromethylisoxazole

The same reaction as described in Preparation 21 was carried out except that 5-dimethylamino-3-methyl-1,2,4-oxadiazole (18.51 g, 0.145 mole) was used. The reaction mixture was allowed to warm to room temperature and tetrahydrofuran and n-hexane were evaporated under reduced pressure. Cold 2N hydrochloric acid (346 ml, 0.652 mole) was added to the residue to neutralize and the mixture was then extracted with diethyl ether. Diethyl ether was evaporated under reduced pressure and the resulting residue was heated for 70 minutes, while low boiling point materials were distilled off by heating to 90° C., to give 32.56 g of crystals. This product was recrystallized from benzene to give the title compound (24.35 g). The mother liquor was purified by column chromatography on silica gel to give the title compound (5.10 g) as crystals. Yield: 91%.

This compound was sublimed at 106°–110° C./0.3 mmHg.

PREPARATION 31

3-Dimethylcarbamoyl-4-phenyl-5-trifluoromethylisoxazole

The same reaction as described in Preparation 21 was carried out except that 3-benzyl-5-dimethylamino-1,2,4-oxadiazole (5.08 g, 0.025 mole) was used. The reaction mixture was allowed to warm to room temperature and then heated under reflux for 1 hour. After cooling, 1N hydrochloric acid (125 ml) was added to the reaction mixture and tetrahydrofuran and n-hexane were then evaporated under pressure. Water (100 ml) was added to the residue and the mixture was extracted with methylene chloride. The extract was washed successively with a 5% solution of sodium hydroxide and a saturated aqueous sodium chloride and dried with anhydrous sodium sulfate. The solvent was evaporated under reduced pressure and the purification of the residue by column chromatography on silica gel was repeated to give the title compound as colorless neeldes. Yield: 3.75 g (48.7%), m.p. 138°–139° C. (dec.).

PREPARATIONS 32 TO 38

The reactions in Preparations 32 to 34 were carried out according to the same procedure as described in Preparation 30 and the reactions in Preparations 35 to 38 were carried out according to the same procedure as described in Preparation 31 to give the following compounds. The results are shown in Table 5.

TABLE 5

| Prep. No. | Starting material 1 g (mole) | Starting material 2 | Product | Yield g (%) | Crystal form m.p. °C. |
|---|---|---|---|---|---|
| 32 | 5-dimethylamaino-3-methyl-1,2,4-oxadiazole 23.00 (0.18) | ethyl trifluoroacetate | 3-dimethylcarbamoyl-amino-5-trifluoro-methylisoxazole | 15.57 (38.7) | — |
| 33 | 5-dimethylamino-3-methyl-1,2,4-oxadiazole 16.63 (0.13) | methyl trifluoroacetate | 3-dimethylcarbamoyl-amino-5-trifluoro-methylisoxazole | 12.54 (43.2) | — |
| 34 | 5-dimethylamino-3-methyl-1,2,4-oxadiazole 9.16 (0.072) | t-butyl pentafluoropropionate | 3-dimethylcarbamoyl-amino-5-pentafluoro-ethylisoxazole | 19.03 (99.5) | — |
| 35 | 5-dimethylamino-3-ethyl-1,2,4-oxadiazole 1.43 (0.01) | methyl trifluoroacetate | 3-dimethylcarbamoyl-amino-4-methyl-5-tri-fluoromethylisoxazole | 2.00 (purity 17%) (14.5) | colorless needles 128–129 |
| 36 | 5-dimethylamino-3-ethyl-1,2,4-oxadiazole 1.43 (0.01) | ethyl pentafluoropropionate | 3-dimethylcarbamoyl-amino-4-methyl-5-pentafluoroethylisoxazle | 0.63 (22.0) | colorless needles 92.5–93.5 |
| 37 | 3-benzyl-5-dimethyl-amino-1,2,4-isoxazole 2.03 (0.01) | t-butyl trifluoroacetate | 3-dimethylcarbamoyl-amino-4-phenyl-5-trifluoromethylisoxazole | 0.345 (11.5) | — |
| 38 | 3-benzyl-5-dimethyl-amino-1,2,4-oxadiazole 7.11 (0.035) | ethyl pentafluoropropionate | 3-dimethylcarbamoyl-amino-4-phenyl-5-pentafluoroethyl-isoxazole | 4.35 (33.7) | colorless needles 99–100 |

PREPARATION 39

3-Phthalimino-5-trifluoromethylisoxazole

A mixture of 3-dimethylcarbamoylamino-5-trifluoromethylisoxazole (2.26 g, 0.010 mole) and phthalic anhydride (3.26 g, 0.022 mole, 2.2 eq.) was heated with stirring at 130° C. for 40 minutes (the reaction mixture was liquefied in the course of the reaction and then solidified again) and then cooled to room temperature. The reaction mixture was dissolved in methylene chloride (30 ml), shaked with a 8% solution of sodium bicarbonate (30 ml) and then washed with water (30 ml). The aqueous sodium bicarbonate and the water layer were extracted with methylene chloride (30 ml) and the extract was combined with the initial solution of methylene chloride. Methylene chloride was evaporated under reduced pressure to give crude crystals (2.80 g). These crude crystals were recrystallized from benzene to give the title compound (2.30 g) as colorless needles. The mother liquor was purified by column chromatography on silica gel to give the title compound (0.37 g) as crystals. Yield: 94.6%, m.p. 161.0°–162.5° C.

Anal. Calcd. for $C_{12}H_5N_2O_3F_3$: C 51.08; H, 1.79; N, 9.93. Found: C, 50.87; H, 1.99; N, 10.10.

1,3-Di(5-trifluoromethyl-3-isoxazole)urea (45 mg, 2.7%) was also obtained as colorless flakes. m.p. 245°° C. (dec.).

PREPARATIONS 40 TO 42

According to the same procedure as described in Preparation 39, the following compounds were prepared. The results are shown in Table 6.

In the table, the starting compound represents the compound of the formula:

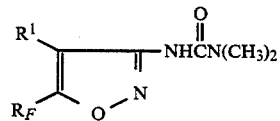

the product represents the compound of the formula:

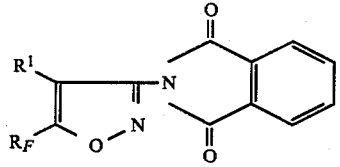

and the by-product represents the compound of the formula:

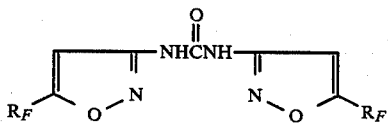

TABLE 6

| | Starting material | | | Yield of product mg (%) | Crystal form m.p. (°C.) | Elemental analysis (calcd./found) | | | By-product | |
|---|---|---|---|---|---|---|---|---|---|---|
| Prep. No. | $R_F$ | $R^1$ | Amount of use g (mmole) | | | C | H | N | Yield (g) (%) | Crystal form m.p. (°C.) |
| 40 | $C_2F_5-$ | H | 2.73 (10.0) | 3.17 (95.5) | colorless needles | 47.00 47.29 | 1.52 1.69 | 8.43 8.18 | 77 (3.6) | colorless prisms |

TABLE 6-continued

| Prep. No. | Starting material $R_F$ | $R^1$ | Amount of use g (mmole) | Yield of product mg (%) | Crystal form m.p. (°C.) | Elemental analysis (calcd./found) C | H | N | By-product Yield (g) (%) | Crystal form m.p. (°C.) |
|---|---|---|---|---|---|---|---|---|---|---|
| 41 | $C_3F_7-$ | H | 3.23 (10.0) | 3.56 (93.2) | 157.0–158.0 colorless plates | 44.00 43.98 | 1.32 1.43 | 7.33 7.29 | 4.7 (1.8) | 176.0–178.0 colorless prisms 156.0–157.0 |
| 42 | $CF_3$<br>\|<br>$CH_3CHCH_2-$ | H | 0.874 (3.30) | 0.987 (92.4) | 129.5–130.0 colorless flakes 125.5–126.5 | 55.56 55.78 | 3.42 3.47 | 8.64 8.66 | — | — |

PREPARATION 43

5-Trifluoromethyl-3-(2-(methoxycarbonyl)benzoyl-)aminoisoxazole

Methanol (10 ml) was added to 3-phthalimino-5-trifluoromethylisoxazole (2.82 g, 0.010 mole) and the mixture was heated under reflux for 1 hour. Methanol was then evaporated under redced pressure and the residue was recrystallized from a mixture of benzene and cyclohexane to give the title compound as colorless needles. This compound decomposed in a silica gel column. Yield: 3.07 g (97.8%), m.p. 116°–117° C.

Anal. Calcd. for $C_{13}H_9N_2O_4F_3$: C, 49.69; H, 2.89; N, 8.92. Found: C, 49.73; H, 3.02; N, 9.00.

PREPARATION 44

5-Pentafluoroethyl-3-(2-(methoxycarbonyl)benzoyl-)aminoisoxazole

The title compound was obtained as colorless prisms according to the same procedure as described in Preparation 43 except that 3-phthalimino-5-pentafluoroethylisoxazole was used. Yield: 59.4%, m.p. 97°–100° C.

Anal. Calcd. for $C_{14}H_9N_2O_4F_5$: C, 46.17; H, 2.49; N, 7.69. Found: C, 46.11; H, 2.62; N, 7.68.

EXAMPLE 34

5-Trifluoromethyl-3-aminoisoxazole

In methanol (15 ml) was dissolved 5-trifluoromethyl-3-(2-(methoxycarbonyl)benzoyl)aminoisoxazole (1.57 g, 0.0050 mole) and 90% hydrazine hydrate (0.42 g, 0.0075 mole) was added to the solution. It was allowed to stand to room temperature for 46 hours. Water (30 ml) was added to it and the mixture was stirred at room temperature for 15 minutes. Crystals were filtered off. The filtered off crystals were washed repeatedly with methylene chloride (45 ml) and the filtrate was extracted with these washings. The filtrate was further extracted with methylene chloride (45 ml×2) and the solvent was distilled off from the combined extract at atmospheric pressure by using a distillation apparatus equipped with a fractionating column packed with glass raschig rings (15 mm in diameter, 200 mm in length). The residue was purified by column chromatography on silica gel to give the title compound. Yield: 0.714 g (93.9%).

EXAMPLE 35

5-Pentafluoroethyl-3-aminoisoxazole

The title compound was obtained in a 95.7% yield according to the same procedure as described in Example 34 except that 5-pentafluoromethyl-3-(2-(methoxycarbonyl)benzoyl)aminoisoxazole was used and reflux was carried out for 45 minutes.

EXAMPLE 36

5-Trifluoromethyl-3-aminoisoxazole

Methanol (20 ml) and 90% hydrazine hydrate (1.67 g, 0.030 mole) were added to 3-phthalimino-5-trifluoromethylisoxazole (5.63 g, 0.020 mole). After stirring at room temperature for 10 minutes, the mixture was heated under reflux and reacted for 45 minutes. After cooling, water (40 ml) was added and the mixture was stirred at room temperature for 15 minutes. The precipitated crystals were filtered off. The crystals were washed with methylene chloride (60 ml) and the filtrate was washed with the washings. It was further extracted with methylene chloride (60 ml×2). The combined extract was distilled off at atmospheric pressure by using a distillation apparatus equipped with a fractionating column packed with glass raschig ring (15 mm in diameter, 200 mm in length). The residue was then distilled under reduced pressure at room temperature to give the title compound as colorless plates (if the solvents were distilled under reduced pressure, the yield lowered for the volatility of the desired product).

Yield: 2.84 g (93.4%), m.p. 44°–45° C., b.p. 79° C./10 mmHg.

EXAMPLES 37 to 45

The reactions in Examples 37 to 45 were carried out according to the same procedure as described in Example 36. The results are shown in Table 7. In the table, the starting material represents the compound of the formula:

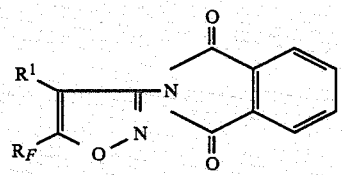

and the product represents the compound of the formula:

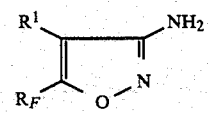

TABLE 7

| Ex. No. | Starting material $R_F$ | $R^1$ | Amount of use g (mole) | Solvent | Rea. temp. | Rea. time (hr.) | Yield of product g (%) | Crystal form m.p. (°C.) b.p. (°C./mmHg) |
|---|---|---|---|---|---|---|---|---|
| 37 | $CF_3$ | H | 2.82 (0.010) | benzene | room temp. | 6 | 0.99 (65.0) | — |
| 38 | $CF_3$ | H | 2.82 (0.010) | benzene | room temp. | 4 | 1.28 (84.2) | — |
| 39 | $CF_3$ | H | 2.82 (0.010) | methylene chloride | room temp. | 4 | 1.36 (89.4) | — |
| 40 | $CF_3$ | H | 2.82 (0.010) | methanol | room temp. | 22.5 | 1.45 (95.4) | — |
| 41 | $CF_3$ | H | 2.82 (0.010) | methanol | reflux | 1 | 1.46 (96.0) | — |
| 42 | $C_2F_5$ | H | 3.32 (0.010) | methanol | room temp. | 87 | 1.98 (98.0) | colorless crystals 56.0–57.5 85–86/9.5 |
| 43 | $C_2F_5$ | H | 3.32 (0.010) | benzene | room temp. | 4 | 1.69 (83.7) | — |
| 44 | $C_3F_7$ | H | 3.25 (0.0085) | methanol | reflux | 0.75 | 2.11 (98.6) | colorless crystals 72.5–74.5 92–93/9.5 |
| 45 | $CF_3$ $CHCH_2$— $CH_3$ | H | 0.9404 (0.0029) | methanol | reflux | 1 | 0.558 (99.1) | colorless crystals 72.0–73.0 — |

EXAMPLE 46

5-Trifluoromethyl-3-aminoisoxazole

Phthalic anhydride (6.52 g, 0.044 mole) was added to 5-trifluoromehtyl-3-dimethylcarbonylaminoisoxazole (4.46 g, 0.020 mole) and the mixture was heated at 130° C. for 40 minutes. After cooling, methanol (20 ml) and hydrazine hydrate (1.89 g, 0.034 mole) wereadded. The mixture was stirred at room temperature for 10 minutes and then heated under reflux for 45 minutes. After cooling, water (40 ml) was added and the mixture was stirred at room temperature for 15 minutes. The title compound (2.77 g, 91.1%) was obtained according to the same work up as described in Example 36. 1,3-Di(5-trifluoromethyl-3-isoxazolyl)urea (2.8 was also obtained.

EXAMPLES 47 to 49

The reactions in Examples 47 to 49 were carried out according to the same procedure as described in Example 46 except that the molar ratio of hydrazine hydrate to a starting material was changed. The results are shown in Table 8. In the table, the starting material represents the compound of the formula:

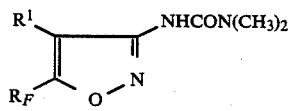

the product represents the compound of the formula:

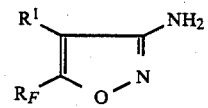

and the by-product 1, 2 and 3, respectively, represent the compound of the formula:

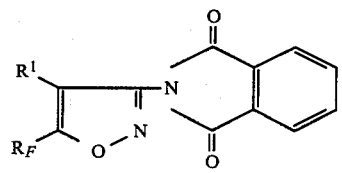

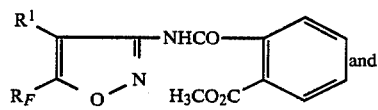

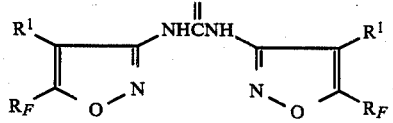

TABLE 8

| Ex. No. | Starting material $R_F$ | $R^1$ | $NH_2NH_2$ $H_2O$ molar ratio | Product % | By-product 1 % | By-product 2 % | By-product 3 % |
|---|---|---|---|---|---|---|---|
| 47 | $CF_3$ | H | 1.3 | 79.6 | 11.4 | 6.3 | 1.6 |
| 48 | $CF_3$ | H | 1.5 | 85.5 | 4.1 | 2.9 | 1.1 |
| 49 | $C_2F_5$ | H | 1.7 | 88.1 | 0.0 | trace | — |

EXAMPLE 50

5-Trifluoromethyl-3-aminoisoxazole

A mixture of 5-trifluormethyl-3-dimethylcarbamoylaminoisoxazole (1.15 g, 0.005 mole) and 36% hydrochloric acid (10 eq.) were reacted at 100° C. for 10 hours. The reaction mixture was worked up in the usual way to give the crude title compound. Crude yield: 0.20 g (26%).

EXAMPLES 51 to 64

The reactions in Examples 51 to 64 were carried out according to the same procedure as described in Example 50. The results are shown in Table 9.

In the table, the starting material represents the compound of the formula:

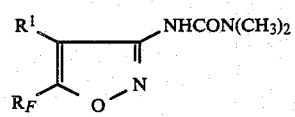

and the product represents the compound of the formula:

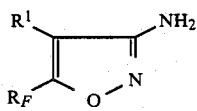

and dry tetrahydrofuran (8 ml) was added dropwise to it below $-75°$ C. over 45 minutes. After stirring at $-75°$ C. for 1 hour, the cooling bath was removed. When the temperature of the reaction mixture reached to 0° C. over 1 hour, it was cooled again to $-25°$ C. and cold 2N hydrochloric acid (19 ml, 35.8 mmole) was added to neutralize it. The reaction mixture was then worked up to obtain crude crystals (2.5363 g), according to the same procedure as described in Example 65. A part (0.6184 g) of this product was purified by column chromatography on silica gel to give pale brown crystals (0.4973 g), m.p. 71°–76° C. The composition etc. of this product are shown in Table 10. These pale brown crystals (0.2289 g) were further recrystallized from acetone/n-hexane to give the title compound as colorless needles. Yield: 0.1328 g, m.p. 71.0°–81.0° C.

NMR ($d_6$-DMSO, $\delta$): 3.20 (s, 2H, $-CH_2-$), 7.17 (s, 2H, $-C(OH)_2-$), 7.4–7.8 (m, 3H, $-C_6H_5$), 8.0–8.2 (m, 2H, $-C_6H_5$).

IR (CHCl$_3$, cm$^{-1}$): 3560, 3350$^{br.}$ (OH), 1565 (C=N).

Anal. Calcd. for $C_{11}H_9N_2O_3F_3$: C, 48.18; H, 3.31; N, 10.22. Found: C, 48.05; H, 3.48; N, 10.49.

After the title compound was dissolved in CDCl$_3$ and 5 hours passed, it became to the mixture of product 1 (28.8 w/w %), 2 (9.6 w/w %) and 3 (61.6 w/w %)

TABLE 9

| Ex. No. | Starting material $R_F$ | $R^1$ | Amount of use g (mmole) | Solvent (1.0 mole/l) | 36% HCl (eq.) | Reaction condition Temp. (°C.) | Time (hr) | Product (after a vacuum distillation) Yield g (%) | b.p. (°C./mmHg) m.p. (°C.) |
|---|---|---|---|---|---|---|---|---|---|
| 51 | CF$_3$ | H | 2.23 (10.0) | ethylene glycol | 2.5 | 100 | 18 | 1.26 (82.9) | 80–81/11 44–45 |
| 52 | CF$_3$ | H | 2.23 (10.0) | ethylene glycol | 2.5 | 100 | 24 | 1.32 (86.8) | 80–81/11 44–45 |
| 53 | CF$_3$ | H | 2.23 (10.0) | ethylene glycol | 2.5 | 100 | 30 | 1.30 (85.5) | 80–81/11 44–45 |
| 54 | CF$_3$ | H | 2.23 (10.0) | ethylene glycol | 2.5 | 100 | 36 | 1.29 (84.8) | 80–81/11 44–45 |
| 55 | CF$_3$ | H | 2.23 (10.0) | ethylene glycol | 5.0 | 100 | 36 | 0.86 (56.6) | 80–81/11 44–45 |
| 56 | CF$_3$ | H | 2.23 (10.0) | ethylene glycol | 10.0 | 100 | 36 | — (<40.0)*[1] | 80–81/11 44–45 |
| 57 | CF$_3$ | H | 2.23 (10.0) | isopropanol | 10.0 | reflux | 40 | 0.87*[2] (57.2) | 80–81/11 44–45 |
| 58 | CF$_3$ | H | 3.50 (15.7) | water | 10.0 | 100 | 16 | 0.89*[3] (37.0) | 80–81/11 44–45 |
| 59 | C$_2$F$_5$ | H | 2.73 (10.0) | ethylene glycol | 2.5 | 100 | 24 | 1.91 (94.5) | 84–85/11.0 56.0–56.5 |
| 60 | n-C$_3$F$_7$ | H | 3.23 (10.0) | ethylene glycol | 2.5 | 100 | 24 | 2.16 (85.7) | 100–101/15.0 72.5–74.0 |
| 61 | CF$_3$ | CH$_3$ | 2.37 (10.0) | ethylene glycol | 2.5 | 100 | 24 | 1.64 (98.7) | 97–98/12.0 35–36 |
| 62 | C$_2$F$_5$ | CH$_3$ | 2.87 (10.0) | ethylene glycol | 2.5 | 100 | 24 | 2.12 (98.1) | 99–100/12.0 32–34 |
| 63 | CF$_3$ | C$_6$H$_5$ | 2.99 (10.0) | ethylene glycol | 2.5 | 100 | 24 | 2.26 (99.0) | — 92–93 |
| 64 | C$_2$F$_5$ | C$_6$H$_5$ | 3.49 (10.0) | ethylene glycol | 2.5 | 100 | 24 | 2.70 (97.1) | — 83–84 |

*[1]NMR determination
*[2]yield after the purification by column chromatography on silica gel (%)
*[3]crude yield (%)

PREPARATION 45

3-(2,2-Dihydroxy-2-trifluoromethyl)ethyl-5phenyl-1,2,4-oxadiazole

Diisopropylamine (molecular sieves 3A dried, 1.86 g, 18.4 mmole) was dissolved in tetrahydrofuran (molecular sieves 4A dried, 16 ml) and the solution was cooled to $-60°$ C. To this solution was added a solution of n-butyllithium in n-hexane (11.1 ml, 17.6 mmole) and it was stirred at 0° C. for 30 minutes. The reaction mixture was cooled to $-75°$ C. and a solution of 3-methyl-5-phenyl-1,2,4-isoxazole (1.28 g, 8.0 mmole), prepared previously, t-butyl trifluoroacetate (2.04 g, 12.0 mmole)

shown in Table 10, but it was stable in $d_6$-DMSO.

PREPARATION 46

3-(2,2-Dihydroxy-2-trifluoromethyl)ethyl-5-t-butyl-1,2,4-oxadiazole

Crude crystals (2.8084 g) were obtained according to the same procedure as described in Preparation 45 except that 3-methyl-5-t-butyl-1,2,4-oxadiazole (1.40 g, 10.0 mmole), t-butyl trifluoroacetate (2.55 g, 15.0 mmole), diisopropylamine (2.33 g, 23.0 mmole), a solution of n-butyllithium in n-hexane (13.8 ml, 22.0 mmole)

and tetrahydrofuran (20 ml) were used. A part (1.4209 g) of this product was purified by column chromatogrpahy on silica gel to give tan crystals (1.1106 g). The composition etc. of this product are shown in Table 10. These tan crystals (0.8852 g) were further recrystallized from benzene/n-hexane to give the title compound as colorless plates. Yield: 0.2895 g, m.p. 59.0°–67.0° C.

NMR (d6-DMSO, δ): 1.37 (s, 9H,

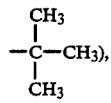

3.08 (s, 2H, —CH2—), 7.08 (s, 2H, —C(OH)2—).

IR (CHCl3, cm$^{-1}$): 3560, 3330$^{br.}$ (OH), 1570 (C=N).

Anal. Calcd. for C9H13N2O3F3: C, 42.52; H, 5.15; N, 11.02. Found: C, 42,43; H, 5.09; N, 11.16.

After the title compound was dissolved in CDCl3 and 5 hours passed, it became to the mixture of product 1 (31.6 w/w %), 2 (7.6 w/w %) and 3 (60.8 w/w %) shown in Table 10, but it was stable in d6-DMSO.

PREPARATION 47

3-(2,2-Dihydroxy-2-trifluoromethyl)ethyl-5-trichloromethyl-1,2,4-oxadiazole

The crude title compound was obtained according to the same procedure as described in Preparation 45 except that 3-methyl-5-trichloromethyl-1,2,4-oxadiazole (2.01 g, 10.0 mmole) was used. The composition etc. of this compound are shown in Table 10.

In table 10, product 1, 2 and 3, respectively, represent

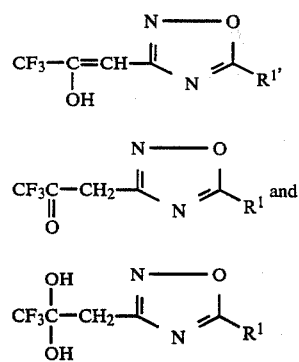

and converted yield represents the value calculated from NMR determination.

(a) Dimethylsulfoxide (molecular sieve 4A dried, 0.46 ml) was added to the pale brown crystals (0.2291 g, 0.864 mmole) obtained from Preparation 45, with stirring and the mixture was heated at 90° C. for 1.5 hours. After cooling to room temperature, water (10 ml) was added thereto and it was extracted with methylene chloride. The extract was dried with anhydrous sodium sulfate and the solvent was evaporated from the extract to give the crude title compound (0.39 g). This product was purified by column chromatogrpahy on silica gel to give the title compound (0.1765 g, 79.5%). The compound was further recrystallized from benzene to give the title compound (0.1354 g) as colorless columns, m.p. 151.5°–153.5° C. The structure of this compound was confirmed by IR and NMR.

(b) The title compound was obtained according to the same procedure as described in (a) except that the compound (0.1371 g, 0.500 mmole) obtain from Preparation 45 and dimethylsulfoxide (0.27 ml) were used. Yield: 0.1013 g (79.1%). The structure of this product was confirmed by IR.

PREPARATION 49

5-Trifluoromethyl-3-pivaloylaminoisoxazole (a) The title compound was obtained according to the same procedure as described in Preparation 48(a) except the tan crystals (1.1402 g, 4.69 mmole) obtained from Preparation 46 was used. Yield: 0.9542 g (86.0%). The structure of this product was confirmed by IR.

(b) The title compound was obtained according to the same procedure as described in Preparation 48(a) except that the compound (0.0582 g, 0.229 mmole) obtained from Preparation 46 and dimethyl sulfoxide (0.12 ml) were used. Yield: 0.0430 g (79.5%). The structure of this product was confirmed by IR.

PREPARATION 50

5-Trifluoromethyl-3-trichloroacetylaminoisoxazole

The title compound was obtained according to the same procedure as described in Preparation 48(a) except that the crude compound (1.1848 g) obtained from Preparation 47 and dimethylsulfoxide (2.4 ml) wre used. Yield: 0.0461 g. This compound was recrystallized from n-hexane to give the title compound as colorless neeldes, m.p. 113.5°–114.5° C. The structure of this product was confirmed by IR and NMR.

EXAMPLE 65

5-Trifluoromethyl-3-aminoisoxazole (a) The reaction was carried out according to the same procedure as described in Example 50 except that

TABLE 10

| Prep. No. | R$^1$ | Product 1 | | Product 2 | | Product 3 | |
|---|---|---|---|---|---|---|---|
| | | Converted yield (%) | $^1$H—NMR(CDCl3,δ) | Converted yield (%) | $^1$H—NMR(CDCl3,δ) | Converted yield (%) | $^1$H—NMR(CDCl3,δ) |
| 45 | C6H5 | 31.8 | 6.21(s,2H,—CH=) 7.4–7.7(m,3H,Ph) 8.0–8.2(m,2H,Ph) 10.50(b.s.,1H,—OH) | 14.1 | 4.25(s,2H,—CH2—) 7.4–7.7(m,3H,Ph) 8.0–8.2(m,2H,Ph) | 47.8 | 3.33(s,2H,—CH2—) 4.79(s,2H,—C(OH)2—) 7.4–7.7(m,3H,Ph) 8.0–8.2(m,2H,Ph) |
| 46 | t-Bu | 48.0 | 1.46(s,9H,—C(CH3)3 6.15(s,1H,—CH=) 10.55(b.s.,1H,—OH) | 11.8 | 1.46(s,9H,—C(CH3)3) 4.19(s,2H,—CH2—) | 30.8 | 1.43(s,9H,—C(CH3)3) 3.25(s,2H,—CH2—) 4.94(b.s.,2H,—C(OH)2—) |
| 47 | —CCl3 | 0.6 | 6.18(s,1H,—CH=) | 0.5 | 4,28(s,2H,—CH2—) | 1.9 | 3.35(s,2H,—CH2—) 4.63(b.s.,2H,—C(OH)2—) |

PREPARATION 48

5-Trifluoromethyl-3-benzoylaminoisoxazole 5-trifluoromethyl-3-benzoylaminoisoxazole (0.8738 g, 3.41 mmole), 36% hydrochloric acid (0.87 g, 8.53 mmole) and ethylene glycol (3.4 ml) were used. The product was then purified by column chromatography on silica gel to give the title compound. Yield: 0.3686 g (75.7%). The structure of this product was confirmed by NMR.

(b) The reaction was carried out according to the same procedure as described in Example 50 except that 5-trifluoromethyl-3-pivaloylaminoisoxazole (0.7553 g, 3.20 mmole), 36% hydrochloric acid (0.81 g, 8.00 mmole) and ehtylene glycol (3.2 ml) were used. The product was then purified by column chromatography on silica gel to give the title compound. Yield: 0.3686 g (75.7%). The structure of this product was confirmed by NMR.

(c) The reaction was carried out according to the same procedure as described in Example 50 except that 5-trifluoromethyl-3-acetylaminoisoxazole (2.21 g, 11.4 mmole), 36% hydrochloric acid (2.89 g, 28.5 mmole) and ehtylene glycol (11.4 ml) were used. The product was then purified by column chromatography on silica gel and further distilled under reduced pressure to give the title compound. Yield: 1.22 g (70.4%), b.p. 84°–85° C./13.0 mmHg.

EXAMPLE 66

3-Trifluoromethyl-4-chloro-5-aminoisoxazole

Acetic acid (7 ml) and anhydrous sodium acetate (0.57 g, 7.00 mmole) were added to 3-trifluoromethyl-5-aminoisoxazole (1.06 g, 7.00 mmole) with stirring at room temperature and a solution of chlorine in carbon tetrachloride (8.5 ml, 1 mole/1, 8.40 mmole) was then added dropwise to the mixture. After stirring for 1 hour at room temperature, the reaction mixture was poured into ice-water (70 ml) and it was adjusted to pH 10 with a solution of sodium hydroxide. It was extracted with methylene chloride. After the extract was dried with anhydrous sodium sulfate, the solvent was distilled off under reduced pressure to give a brown viscous liquid (0.80 g). This product was purified by column chromatography on silica gel to give a dark red liquid (0.54 g). It was further distilled under reduced pressure to give the title compound as a colorless liquid. Yield: 0.41 g (31.5%), b.p. 73.0°–74.5° C./4.0 mmHg. The structure of this product was confirmed with IR and NMR.

EXAMPLE 67

3-Trifluoromethyl-4-bromo-5-aminoisoxazole

The reaction was carried out according to the same procedure as described in Example 66 except that 3-trifluoromethyl-5-aminoisoxazole (1.06 g, 7.00 mmole), acetic acid (7 ml), anhydrous sodium acetate (0.57 g, 7.00 mmole) and bromine (1.34 g, 8.40 mmole) were used. The product was then purified by column chromatography on silica gel to give a yellow liquid (1.24 g). This product was distilled under reduced pressure to give the title compound as a colorless liquid. Yield: 1.07 g (66.2%), b.p. 85.5°–86.5° C./4.0 mmHg. The structure of this product was confirmed by IR and NMR.

EXAMPLE 68

5-Trifluoromethyl-3-methylaminoisoxazole

In dry methylene chloride (20 ml) was dissolved 5-trifluoromethyl-3-aminoisoxazole (3.04 g, 20.0 mmole) and trifluoroacetic anhydride (4.83 g, 23.0 mmole) was added dropwise to the solution while keeping the mixture at room temperature. After stirring at room temperature for 1 hour, precipitated crystals were filtered off to give colorless prisms (1.83 g), m.p. 126°–127° C. This compound is 5-trifluoromethyl-3-trifluoroacetylaminoisoxazole. The filtrate was evaporated under reduced pressure to give additional crystals (3.43 g).

The combined crystals were dissolved in acetone (100 ml). Anhydrous sodium carbonate (6.35 g, 60 mmole) and dimethyl sulfate (5.05 g, 40 mmole) were added to the solution and the mixture was stirred at room temperature for 20 hours. The precipitated crystals were filtered off and the filtrate was evaporated under reduced pressure. The resulting residue was dissolved in benzene. After being washed with a 8% solution of sodium bicarbonate the solvent was evaporated under reduced pressure to give a mixture (2.88 g) of 5-trifluoromethyl-3-N-methyl-N-trifluoroacetylaminoisoxazole and 5-trifluoromethyl-3-methylaminoisoxazole as residue. To this were added methanol (20 ml) and a 5% solution of sodium hydroxide (19.2 g). After standing at room temperature for 15 minutes, the solvent was evaporated under reduced pressure. Methylene chloride was added to the residue and the precipitated crystals were filtered off to give the title compound (2.05 g, 61.7%).

The product was recrystallized from n-hexane to give colorless prisms, m.p. 39.0°–41.0° C.

EXAMPLE 69

3-Trifluoromethyl-4-phenyl-5-methylaminoisoaxasole

The reaction and work up were carried out to obtain colorless prisms according to the same procedure as described in Example 68 except that 3-trifluoromethyl-4-phenyl-5-aminoisoxazole was used. m.p. 119.5°–121.0° C. (recrystallized from n-hexane/benzene).

EXAMPLE 70

5-Pentafluoroethyl-3-methylaminoisoxazole

The reaction and work up were carried out to obtain a colorless liquid according to the same procedure as described in Example 68 except that 5-pentafluoroethyl-3aminoisoxazole was used. b.p. 88° C./12 mmHg.

EXAMPLE 71

3-Trifluoromethyl-5-methylaminoisoxazole

Dry benzene (56 ml) and pyridine (11.85 g, 150 mmole) were added to 3-trifluoromethyl-5-aminoisoxazole (9.12 g, 60.0 mmole) and the mixture was cooled. Acetyl chloride (10.37 g, 132 mmole) was added dropwise to the mixture, while keeping it below 10° C. After being added dropwise, the mixture was stirred with ice cooling for 10 minutes and at room temperature for 1 hour. Water (60 ml) was added and it was stirred for an additional hour. Benzene (60 ml) was added and the mixture was separated. The benzene layer was washed successively with 2% hydrochloric acid (60 ml) and a 8% solution of sodium bicarbonate and the solvent was evaporated under reduced presssure. Methanol (120 ml) and sodium hydroxide (4.80 g 120 mmole) were added to the residue and the mixture was stirred overnight at room temperature. After being neutralized with conc. hydrochloric acid, the solvent was evaporated under reduced pressure and the resulting residue was dissolved by the addition of benzene (100 ml) and ethyl acetate (20 ml). This solution was washed with water (60 ml) and the solvents were evaporated under reduced pressure to give 3-trifluoromethyl-5-acetylaminoisoxazole (9.51 g) as crystals. This product was recrystallized from benzene to give colorless plates. Yield: 5.67 g, m.p. 108.5°–109.5° C.

Sodium metal (0.28 g, 12.3 mmole) was dissolved in dry methanol (12.3 ml) and to this solution was added 3-trifluoromethyl-5-acetylaminoisoxazole (2.38 g, 12.26 mmole). After stirring at room temperature for 15 minutes, the mixture was concentrated in vacuo and dry benzene (12.3 ml) was added to the residue. The mixture was concentrated in vacuo and dry benzene (18.4 ml) and dimethyl sulfate (1.55 g, 12.3 mmole) were added to the residue, followed by refluxing for 2 hours. After cooling, the precipitated crystals were filtered off. The filtrate was washed with a 8% solution of sodium bicarbonate and concentrated in vacuo. A 5% solution of sodium hydroxide (11.8 g) was added to the residue and the mixture was sitrred at room temperature for 2 hours. It was extracted with methylene chloride and the methylene chloride layer was dried with anhydrous sodium sulfate. The extract was concentrated in vacuo and the resulting residue was recrystallized from cyclohexane to give the title compound as colorless columns. Yield: 1.41 g (65.4%). m.p. 48.5°–50.0° C.

What is claimed is:

1. A compound of the formula:

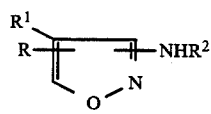

(I)

in which:
R is sufluoro $C_{1-14}$ alkyl; $R^1$ is $C_{1-5}$ alkyl, chlorine, bromine, iodine, phenyl, phenyl substituted with one or an plurality of substituents selected from the group consisting fluorine, shlorine, $C_{1-4}$ alkyl and $C_{1-4}$ alkoxy or phenyl substituted with methylendioxy or ethylene dioxy; and $R^2$ is hydrogen or $C_{1-4}$ alkyl, or a salt of thereof.

2. The compound of claim 1 in which R is located at 5-position and ——$NHR^2$ is located at 3-position.

3. The compound of claim 2 being 5-trifluoromethyl-4-methyl-3-aminoisoxazole.

4. The compound of claim 2 being 5-pentafluoroethyl-4-methyl-3-aminoisoxazole.

5. The compound of claim 2 being 5-trifluoromethyl-4-phenyl-3-aminoisoxazole.

6. The compound of claim 2 being 5-pentafluoroethyl-4-phenyl-3-aminoisoxazole.

7. The compound of claim 2 being 5-trifluromethyl-4 -4-(4-fluorophenyl)-3-aminosoxazole.

8. The compound of claim 2 being 5-trifluoromethyl-4-(4-chlorophenyl)-3-aminoisoxazole.

9. The compound of claim 2 being 5-trifluoromethyl-4-(4-methoxyphenyl)-3-aminoisoxazole.

10. The compound of claim 2 being 5-trifluoromethyl-4-(4-methoxyphenyl)-3-aminoisoxazole.

11. The compound of claim 2 being 5-trifluoromethyl-4-dimethoxyphenyl)-3-aminoisoxazole.

12. The compound of claim 2 being 5-trifluoromethyl-4-(3,4-methylenedioxyphenyl)-3-aminoisoxazole.

13. The compound of claim 1 in which R is located at 3-position and —$NHR^2$ is located at 5-position.

14. The compound of claim 13 being 3-trifluoromethyl-4-methyl-5-aminoisoxazole.

15. The compound of claim 13 being 3-pentafluoroethyl-4-methyl-5aminoisoxazole.

16. The compound of claim 13 being 3-trifluoromethyl-4-phenyl-5-aminoisoxazole.

17. The compound of claim 13 being 3-pentafluoroethyl-4-phenyl-5-aminoisoxazole.

18. The compound of claim 13 being 3-trifluoromethyl-4 -(4-fluorophenyl)-5-aminoisoxazole.

19. The compound of claim 13 being 3-trifluoromethyl-4-(4-chlorophenyl)-5-aminisoxazole.

20. The compound of claim 13 being 3-trifluoromethyl-(4-methylphenyl)-5-aminoisoxazole.

21. The compound of claim 13 being 3-trifluoromethyl-4-(4-methoxyphenyl)-5-aminisoxazole.

22. The compound of claim 13 being 3-trifluoromethyl-(3,4-dimethoxyphenyl)-5-aminoisoxazole.

23. The compound of claim 13 being 4-trifluoromethyl-(3,4-methylenedioxyphenyl)-5-aminisoxazole.

* * * * *